United States Patent [19]
Bakhit et al.

[11] Patent Number: 6,022,732
[45] Date of Patent: Feb. 8, 2000

[54] HYDROGEN PEROXIDE DESTROYING COMPOSITIONS AND METHODS OF USING SAME

[75] Inventors: Peter G. Bakhit, Huntington Beach; Terrence J. Hunt, Anaheim Hills; Michael B. Shah, Orange, all of Calif.

[73] Assignee: Allergan, Waco, Tex.

[21] Appl. No.: 08/827,614

[22] Filed: Apr. 9, 1997

[51] Int. Cl.[7] .............................. D06M 16/00; A62D 3/00; A61K 31/74; A61L 9/00
[52] U.S. Cl. .............................. 435/264; 134/26; 134/42; 252/186.28; 252/186.29; 252/186.42; 424/78.04; 424/94.4; 424/616; 422/30
[58] Field of Search ................................ 435/264; 422/28, 422/30; 252/186.28, 186.29, 186.42, FOR 131; 134/42, 26; 424/78.04, 94.4, 616

[56] References Cited

U.S. PATENT DOCUMENTS

| | | | |
|---|---|---|---|
| Re. 32,672 | 5/1988 | Huth et al. | ................ 252/95 |
| 2,635,069 | 4/1953 | Baker . | |
| 3,123,539 | 3/1964 | Beers, Jr. . | |
| 3,930,953 | 1/1976 | Stark . | |
| 4,585,488 | 4/1986 | Giefer | ................ 134/27 |
| 4,775,424 | 10/1988 | Wisotzki et al. | ................ 134/42 |
| 4,826,658 | 5/1989 | Kay | ................ 422/30 |
| 4,959,212 | 9/1990 | Stancesco et al. | ................ 424/94.1 |
| 5,011,661 | 4/1991 | Schafer et al. | ................ 422/30 |
| 5,145,644 | 9/1992 | Park et al. | ................ 422/28 |
| 5,360,732 | 11/1994 | Berka et al. | ................ 435/192 |
| 5,360,901 | 11/1994 | Berka et al. | ................ 536/23.2 |
| 5,362,647 | 11/1994 | Cook et al. | ................ 435/264 |

FOREIGN PATENT DOCUMENTS

| | | | |
|---|---|---|---|
| 9211041 | 7/1992 | WIPO | ................ A61L 2/18 |
| 9317721 | 10/1993 | WIPO | ................ A61L 2/00 |

*Primary Examiner*—David A. Redding
*Attorney, Agent, or Firm*—Frank J. Uxa

[57] ABSTRACT

Compositions, and methods for using such compositions, which are useful to destroy hydrogen peroxide in a liquid aqueous medium, such as that used to disinfect contact lenses. In one embodiment, the composition comprises a hydrogen peroxide destroying component effective when released in a hydrogen peroxide-containing liquid aqueous medium to destroy or cause the destruction of hydrogen peroxide present in the hydrogen peroxide-containing liquid aqueous medium, and a barrier component acting to substantially prevent the release of the hydrogen peroxide destroying component for a period of time after the composition is initially contacted with the hydrogen peroxide-containing liquid aqueous medium, the barrier component comprising a material selected from the group consisting of water soluble cellulose derivatives and mixtures thereof having a molecular weight of at least about 20,000. The composition results in reduced foam formation relative to a similar composition including a barrier component comprising a similar material having a molecular weight of 10,000 when both the composition and the similar composition are exposed to identical hydrogen peroxide-containing liquid aqueous media to destroy or cause the destruction of the hydrogen peroxide therein.

18 Claims, No Drawings

HYDROGEN PEROXIDE DESTROYING COMPOSITIONS AND METHODS OF USING SAME

BACKGROUND OF THE INVENTION

This invention relates to hydrogen peroxide destroying compositions, and to methods of using the same, which are useful to decrease the concentration of, or even substantially eliminate, hydrogen peroxide present in a liquid medium. More particularly, the invention relates to such compositions, and methods for using such compositions, useful in destroying residual hydrogen peroxide present in a liquid aqueous medium containing a lens, such as a contact lens, which has been disinfected by the action of hydrogen peroxide.

Contact lenses should be periodically disinfected by the user to prevent infection or other deleterious effects on ocular health which may be associated with contact lens wear. Currently, there are several different conventional systems and methods which enable the user to clean and disinfect their contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are hydrogen peroxide disinfection systems. Disinfecting hydrogen peroxide solutions are effective to kill the bacteria and fungi which may contaminate contact lenses. However, residual hydrogen peroxide on a disinfected contact lens may cause irritation, burning or trauma to the eye unless this hydrogen peroxide is destroyed, i.e., decomposed, neutralized, inactivated or chemically reduced. Therefore, the destruction of the residual hydrogen peroxide in the liquid medium containing the disinfected contact lens is needed to enable safe and comfortable wear of the disinfected contact lens. As a further enhancement to comfortable wear of disinfected contact lenses, it would be advantageous to treat the disinfected lens in a high viscosity/lubricity medium before placing the lens in the eye.

Associated with the problem of hydrogen peroxide destruction in contact lens disinfection systems are the problems of easy use and user compliance. To enhance ease of use and user compliance, several efforts have focused on one-step disinfection and hydrogen peroxide destruction. In this regard, various time release tablets containing a core tablet and a totally soluble or insoluble coating have been suggested. In addition, disadvantageous foam formation often occurs as the hydrogen peroxide is being destroyed. This can create liquid spillage and make it less likely for the user to effectively and consistently disinfect his/her lenses.

Schafer et al European Patent Application 86-109,361.5 discloses a hydrogen peroxide neutralizer tablet covered with a water-soluble coating to delay the dissolution of the tablet. This publication discloses the use of various soluble polymers, such as cellulose ethers, which include suitable polyhydric alcohols to control the timed release as a coating for the neutralizer tablet. Kaspar et al U.S. Pat. No. 4,568,517 discloses a one step contact lens disinfecting process which involves hydrogen peroxide and a neutralizer having a hydrogen peroxide neutralizing compound in tablet or particle form and a coating encasing the tablet or particles which acts as a delayed release coating. Among the hydrogen peroxide neutralizing compounds disclosed are peroxidase/catalase enzymes. The coating may be made of organically modified cellulose, such as hydroxypropylmethyl cellulose, ethyl cellulose, cellulose acetate phthalate and hydroxypropyl cellulose. No disclosure is provided as to the specific molecular weights of such polymers or as to how to reduce foam formation.

Park et al U.S. Pat. No. 5,145,644 discloses methods for coating catalase core tablets with cellulose derivatives, such as hydroxypropylmethyl cellulose, using ketone components. Cook et al U.S. Pat. No. 5,362,647 discloses disinfecting contact lenses using hydrogen peroxide with delayed release coated tablets including catalase obtained as the result of the action of *Aspergillus niger* to cause the destruction of the residual hydrogen peroxide. No specifics regarding the molecular weight of the coatings and/or reducing foam formation during hydrogen peroxide destruction are disclosed.

There continues to be a need for one step contact lens disinfecting systems using a hydrogen peroxide destroying component in which excessive foam formation is reduced or even eliminated and a high viscosity/lubricity medium is used prior to placing the disinfected lens in the eye.

SUMMARY OF THE INVENTION

New compositions and methods useful for destroying hydrogen peroxide in a liquid aqueous medium, in particular for destroying residual hydrogen peroxide in a liquid aqueous medium containing a disinfected contact lens, have been discovered. The present invention allows the hydrogen peroxide destroying component or components to be initially contacted with the liquid aqueous medium at the same time the contact lens to be disinfected is initially contacted with the liquid aqueous medium. For example, the present compositions and the contact lens to be disinfected can be added to the liquid aqueous medium at substantially the same time. This feature greatly reduces the amount of user time and care required to effectively disinfect his/her lenses and destroy the residual hydrogen peroxide. Additionally, and importantly, reduced foam formation is obtained during hydrogen peroxide destruction. Further, the viscosity and lubricity of the liquid medium after hydrogen peroxide destruction is advantageously increased, which allows the disinfected lens to be worn with a greater degree of comfort. Thus, enhanced user compliance, more consistent and convenient contact lens disinfection and a greater degree of user comfort and eye safety are provided in a disinfection system which, from the user's point of view, is substantially identical to use relative to the hydrogen peroxide contact lens disinfection system currently in use.

In one broad aspect, the present invention is directed to compositions useful for destroying residual hydrogen peroxide in a hydrogen peroxide-containing liquid aqueous medium, hereinafter referred to as HPLM. The present compositions comprise a hydrogen peroxide destroying component, hereinafter referred to as HPDC, effective when released in a HPLM to destroy or cause the destruction of hydrogen peroxide present in the HPLM; and a barrier component acting to substantially prevent the release of the HPDC in the HPLM for a period of time after the composition is initially contacted with the HPLM. This barrier component comprises a water soluble material selected from water soluble cellulose derivatives and mixtures thereof, having a molecular weight of at least about 20,000. It has been found that the present compositions result in reduced foam formation relative to a similar composition including a barrier component comprising a similar polymeric material having a molecular weight of 10,000 when both the present composition and the similar composition are exposed to identical HPLMs to destroy or cause the destruction of the hydrogen peroxide therein.

Thus, the present invention takes advantage of the unexpected discovery that the use of water soluble cellulose derivatives having high molecular weights, in particular molecular weights of at least about 20,000, result in reduced foam formation relative to compositions including with barrier components including similar materials which have lower molecular weights, such as molecular weights of 10,000. Preferably, the water soluble cellulose derivatives have molecular weights of at least about 40,000 and more preferably at least about 60,000.

Using such high molecular weight cellulose derivatives, as described herein, preferably provides an additional, important advantage in that the liquid aqueous medium in which the cellulose derivatives are dissolved have increased viscosity and lubricity, relative to the same liquid aqueous medium without the cellulose derivatives. Such increased viscosity and lubricity are important in that a disinfected contact lens taken from such a high viscosity/lubricity liquid aqueous medium and placed directly in the wearer's eye is more comfortable to wear, relative to using a lower viscosity/lubricity liquid aqueous medium to treat the disinfected lens just prior to placing the lens in the wearer's eye.

The very useful cellulose derivatives are selected from water soluble cellulose ethers, water soluble cellulose esters and mixtures thereof. A particularly useful cellulose derivative is hydroxypropylmethyl cellulose.

High molecular weight hydroxypropylmethyl cellulose having reduced methoxyl substitution, preferably a methoxyl substitution of less than about 25%, advantageously results in increased water solubility so that the presently useful relatively high molecular weight material is solubilized in the HPLM in a reasonable time, for example, on the order of about 6 hours or less.

The composition preferably further includes an effective amount of a component useful in the composition to facilitate solubilizing the material, for example, to insure that the material is solubilized in the HPLM in a reasonable time.

Although any suitable HPDC may be employed in accordance with the present invention, it is preferred that the HPDC includes catalase. For example, the catalase used may be obtained from mammalian sources, such as bovine livers, or from non-mammalian sources, such as catalase obtained as the result of the action of microorganisms, for example, *Micrococcus luteus, Aspergillus niger* and the like. A particularly useful catalase is that obtained as the result of the action of *Aspergillus niger*. Using *Aspergillus niger* catalase, reduced amounts of the HPDC can be employed to provide for effective destruction of the hydrogen peroxide in the HPLM. Such reduced amounts of HPDC are advantageous to further reduce the foam formation during hydrogen peroxide destruction.

In a particularly useful embodiment, the present composition is in the form of a tablet and includes about 50 International Units to about 2,000 International Units of catalase activity from catalase obtained as the result of the action of *Aspergillus niger*.

The present compositions preferably further comprise at least one enzyme capable of removing at least one form of debris from a contact lens located in the HPLM. Such enzyme can be made to be released into the aqueous liquid medium before, during and/or after the hydrogen peroxide in the liquid aqueous medium is destroyed. A particularly useful composition comprises Subtilisin A as the at least one enzyme, catalase derived as the result of the action of *Aspergillus niger* as the HPDC and hydroxypropylmethyl cellulose as the barrier component material.

In a very useful embodiment, the composition has a layered structure with at least one item comprising the HPDC being substantially coated with a coating comprising the material.

In another broad aspect of the invention, compositions are provided which comprise catalase obtained as the result of the action of *Aspergillus niger* effective when released in a HPLM to cause the destruction of the hydrogen peroxide present in the HPLM, and a barrier component acting to substantially prevent the release of the catalase for a period of time after the composition is initially contacted with the HPLM. The barrier component comprises a water soluble material selected from water soluble cellulose derivatives and mixtures thereof having a molecular weight of at least about 20,000, preferably at least about 40,000 and more preferably at least about 60,000. More preferably, the material is hydroxypropylmethyl cellulose.

In a further broad aspect of the present invention, methods of disinfecting a lens, such as a contact lens, comprise (1) contacting the lens with a HPLM at effective lens disinfecting conditions, thereby disinfecting the lens; and (2) contacting the HPLM with a composition comprising a HPDC effective when released in the HPLM to destroy or cause the destruction of hydrogen peroxide present in the HPLM, and a barrier component acting to substantially prevent the release of the HPDC for a period of time after the composition is initially contacted with the HPLM. The compositions useful in the present invention are as described elsewhere herein.

In an additional broad aspect of the present invention, methods for destroying hydrogen peroxide are provided. Such methods comprise contacting a HPLM with a composition, as described elsewhere herein, at conditions effective to destroy or cause the destruction of hydrogen peroxide present in the HPLM.

These and other aspects of the present invention are apparent in the following detailed description, examples and claims.

DETAILED DESCRIPTION OF THE INVENTION

The present invention is of value where hydrogen peroxide is used to disinfect all types of lenses, e.g., contact lenses, which are benefitted by periodical disinfecting. Such lenses, e.g., conventional contact lenses, in particular soft contact lenses, may be made of any suitable material or combination of materials and may have any suitable configuration not substantially deleteriously affected by hydrogen peroxide, the present compositions or the present methods.

The present invention is particularly useful for destroying residual hydrogen peroxide in a HPLM which has been used to disinfect a contact lens.

The liquid medium used to disinfect a contact lens in the present invention includes a disinfecting amount of hydrogen peroxide. Preferably, a disinfecting amount of hydrogen peroxide means such amount as will reduce the microbial burden by one log in three hours. Still more preferably, the hydrogen peroxide concentration is such that the microbial load is reduced by one log order in one hour. Particularly preferred are those hydrogen peroxide concentrations which reduce the microbial load by one log unit in 10 minutes or less. Relatively mild aqueous hydrogen peroxide solutions, preferably containing about 0.5% to about 6% of hydrogen peroxide (w/v), are known to be effective disinfecting solutions for contact lenses. These solutions are effective at killing bacteria and fungi which may be found on contact lenses. However, once contact lens has been disinfected by being immersed in the HPLM, the residual hydrogen peroxide, e.g., on the lens, should be destroyed so that the lens may be safely and comfortably worn on the eye. If this residual hydrogen peroxide is not destroyed before the lens is worn, irritation to the eye or wearing discomfort may occur.

Thus, the present compositions, which are preferably initially contacted with the HPLM at substantially the same time as is the contact lens to be disinfected, allow for effective lens disinfection and, in addition, effectively destroy the residual hydrogen peroxide remaining in the HPLM so that the disinfected lens can be removed from the liquid medium and placed into the eye for safe and comfortable wear. The present compositions are preferably present in the form of a tablet, although other forms, such as pills, particles, microgranules, powders and the like, may be employed. The compositions preferably include at least one coated item, for example, a layered tablet, a layered particle, a coated microgranule and the like, each of which includes an item, for example, a core such as a core tablet, including a HPDC and a coating of a barrier component. The barrier component comprises a water soluble material selected from water soluble cellulose derivatives and mixtures thereof, preferably substantially surrounding the item which includes the HPDC. The item or items are preferably about 40% to about 99% by weight of the total of the item or items plus barrier component, while the barrier component is preferably about 1% to about 60% by weight of the total of the item or items plus barrier component.

The present invention is based at least in part on the discovery that the molecular weight of water soluble polymeric barrier components which delay the release of HPDCs in HPLMs affects the degree of foam formation as the hydrogen peroxide in the HPLMs is being destroyed. It has been unexpectedly found that higher molecular weight, water soluble polymeric barrier components, such a cellulose derivatives, result in reduced foam formation relative to similar barrier components having lower molecular weights. Cellulose derivatives which have molecular weights of at least about 20,000 are preferred, with molecular weights of at least about 40,000 or at least about 60,000 being more preferred.

The water soluble barrier components useful in the present invention includes those materials which dissolve in water over a period of time. The barrier component or components chosen for use should have no substantial detrimental effect on the lens being treated, on the disinfecting and cleaning of the lens, or on the person in whose eye the disinfected/cleaned lens is to be placed. The barrier component or components used in the present compositions and the amount or thickness of the barrier component are preferably chosen so that the barrier component dissolves into the HPLM at a rate so that the HPDC is released in the HPLM after a period of time sufficient for the hydrogen peroxide to disinfect the lens located in the HPLM.

The water soluble cellulose derivatives useful in the present invention can be obtained by derivatizing cellulose to achieve the desired degree of water solubility. Substituent groups selected from hydrocarbyl groups and substituted hydrocarbyl groups are particularly useful for inclusion in the present cellulose derivatives. Such substituents which include 1 to about 10 carbon atoms, and such groups which include a polar group, such as a hydroxyl group, a carbonyl group, a carboxyl group and the like, are very effective in providing cellulose derivatives with the desired water solubility. Such water soluble cellulose derivatives can be produced using conventional and well known organic synthesis techniques.

In one embodiment, the water soluble cellulose derivatives are selected from water soluble cellulose ethers, water soluble cellulose esters and mixtures thereof, preferably water soluble cellulose ethers and mixtures thereof. Examples of water soluble cellulose esters include cellulose acetate phthalate, hydroxypropylmethyl cellulose phthalate and the like.

Water soluble alkyl ethers and/or hydroxyalkyl ethers of cellulose are among the water soluble cellulose ethers which can be employed. The alkyl groups preferably have 1 to about 6, more preferably 1 to about 3 or 4, carbon atoms. Specific examples of useful water soluble cellulose ethers include hydroxypropylmethyl cellulose, ethyl cellulose, methyl cellulose, hydroxyethylmethyl cellulose, hydroxypropyl cellulose, hydroxyethyl cellulose, metal, in particular alkali metal, salts of cellulose ethers such as sodium carboxymethyl cellulose, and the like and mixtures thereof.

A particularly useful water soluble cellulose derivative is hydroxypropylmethyl cellulose.

Although the high molecular weight cellulose derivatives useful in the present invention are water soluble, it may be advantageous to take measures to further enhance and/or control the solubility of such materials. For example, the amounts of such materials used in the present compositions is preferably controlled to provide the desired delayed release periods of time. As noted above, the degree of substitution of the high molecular weight cellulose derivatives may be used to control water solubility. In one particular embodiment, when high molecular weight hydroxyproplymethyl cellulose is used, such material preferably has a methoxyl substitution of less than about 30%, more preferably less than about 25% at a hydroxypropoxyl substitution of about 7 to 12%. Such materials have been found to dissolve in water in an advantageously reasonable time.

In addition, the present compositions, in particular the present barrier components, preferably include effective, more preferably minor (that is less than about 50% by weight of the barrier component) effective, amounts of components useful in the composition to facilitate solubilizing the high molecular weight cellulose derivatives. Such components include any suitable, e.g., ophthalmically acceptable, substances which function to affect the water solubility of the high molecular weight cellulose derivatives, as desired. Such components include, for example, low molecular weight cellulose derivatives, other low molecular weight polymeric materials, such as polyalkylene glycols, sugars, such as sucrose, etc., and the like and mixtures thereof. The low molecular weight cellulose derivatives preferably have a molecular weight which is reduced relative to the molecular weight of the cellulose derivative or derivatives which are present as the major constituent, that is more than about 50% by weight, of the barrier component. For example, if the major constituent has a molecular weight of about 80,000, the "low molecular weight" minor constituent preferably has a molecular weight of about 40,000 or less. Very useful polyalkylene glycols include polyethylene glycols, preferably having molecular weights in the range of about 500 to about 10,000.

Any suitable HPDC may be included in the present compositions. Such HPDCs should effectively destroy the residual hydrogen peroxide and have no undue detrimental effect on the disinfected lens or on the eye into which the disinfected lens is placed. Among the useful HPDCs are hydrogen peroxide reducing agents, enzymes useful to destroy hydrogen peroxide, such as peroxidases and catalase, and mixtures thereof.

Examples of the hydrogen peroxide reducing agents which are useful in the present invention are alkali metal in particular sodium, thiosulfates; thiourea; alkali metal, in particular sodium, sulfites; thioglycerol; N-acetylcysteine alkali metal, in particular sodium, formates; ascorbic acid; isoascorbic acid; glyoxylic acid; pyruvic acid; ophthalmically acceptable salts, such as alkali metal and in particular sodium salts, of such acids; mixtures thereof and the like.

A particularly useful HPDC is catalase since it is often effective to substantially eliminate hydrogen peroxide from a liquid medium in a reasonable period of time, for example, on the order of about 1 minute to about 12 hours, preferably about 5 minutes to about 1 hour, after being initially released in the HPLM. As noted above, catalases obtained from mammalian sources and/or non-mammalian sources can be employed.

The presently useful catalases preferably have kinetic properties which facilitate their use in the present invention. Specifically, such useful catalases preferably have an acceptably low rate of causing the destruction of hydrogen peroxide, and/or an acceptably high resistance to oxidation by hydrogen peroxide so that reduced or low amounts of the catalase can be employed in the present invention, thereby further reducing or inhibiting foam formation during hydrogen peroxide destruction. Catalases, in particular catalases from other than mammalian sources, such as catalases obtained as the result of the action of microorganisms, which have relatively high pI's, for example, a pI of at least about 5.0, are preferred and have advantages, in particular have enhanced shelf stability, e.g., longer effective shelf life, relative to catalases with relatively low pI's. As used herein, the term "pI" refers to the pH at which any given catalase is neutral. In general, the higher the pI is the more basic the catalase is.

In addition, the catalases useful in the present invention preferably have a substantial degree of stability in the presence of hydrogen peroxide. Such stability is advantageous so that relatively low concentrations of catalase are effective to cause the destruction of at least about 95%, preferably substantially all, of the hydrogen peroxide in HPLM containing the disinfected contact lens. The stability of a catalase in the presence of hydrogen peroxide is inversely proportional to the rate constant, $k_2$, of the reaction in which the catalase is oxidized by hydrogen peroxide. That is, the lower the $k_2$ of a catalase, the higher the stability of the catalase in the presence of hydrogen peroxide. For example, the $k_2$ for conventional bovine catalase is 8.9, while the $k_2$ for catalase obtained as the result of the action of *Aspergillus niger* is 0.51. These $k_2$ values are reported in De Luca et al, "Inactivation of an Animal and a Fungal Catalase by Hydrogen Peroxide", Archives of Biochemistry and Biophysics, Vol. 320, No. 1, pp. 129–134, 1955, which is incorporated in its entirety herein by reference.

The presently useful catalases preferably have $k_2$'s of about 2.0 or less, more preferably about 0.75 or less.

A particularly useful catalase in accordance with the present invention is catalase obtained as the result of the action of *Aspergillus niger*, more preferably such a catalase having a pI of at least about 5.0. Catalase obtained from the action of *Aspergillus niger* and sold by NOVO is still more preferred.

The amount of HPDC employed is preferably sufficient to destroy all the hydrogen peroxide present in the HPLM into which the HPDC is placed. Excess HPDC may be employed. Very large excesses of HPDC are to be avoided since the HPDC itself may cause problems with the disinfected contact lens and/or the ability to safely and comfortably wear such disinfected contact lens. When catalase is employed as a HPDC, it is preferably present in an amount of about 10 to about 1000, more preferably about 10 to about 700, International Units of catalase activity per milliliter of liquid medium containing 3% (w/v) of hydrogen peroxide contacted with catalase-containing composition to cause the destruction of the hydrogen peroxide therein. Still more preferably, when catalase obtained as the result of the action of *Aspergillus niger* is employed, it is present in an amount of about 10 to about 200 International Units of catalase activity per milliliter of liquid medium containing 3% (w/v) of hydrogen peroxide contacted with the catalase containing composition to cause the destruction of the hydrogen peroxide therein.

The present compositions can be, and preferably are, provided as tablets, pills or other single dosage or use forms suitable for destroying or causing the destruction of hydrogen peroxide in a HPLM used to disinfect a single pair of contact lenses, for example, about 3 to 10 milliliters of a HPLM containing 3% (w/v) of hydrogen peroxide. When catalase is employed as a HPDC, each single dosage form preferably includes about 50 to about 10,000 International Units of catalase activity. When catalase obtained as the result of the action of *Aspergillus niger* is employed, it is preferably present in an amount of about 50 to about 2000 International Units of catalase activity per single dosage form.

The HPDC may be combined with one or more other components, for example, in the at least one item or core of the present compositions. Such other components may include, for example, fillers, binders, tonicity agents, contact lens conditioning/wetting agents, buffering agents, lubricating agents and the like. Each of these components may be present, if at all, in an amount effective to perform its designated function or functions. Examples of each of these types of components are conventional and well known in the art. Therefore, a detailed description of such components is not presented here.

An important feature of the present invention is the enhanced lubricity obtained as the result of the high molecular weight barrier materials useful herein. These high molecular weight materials are water soluble and, when dissolved in the liquid aqueous medium, add to the viscosity and lubricity of the liquid relative to the viscosity and lubricity obtained using a similar barrier material having a lower molecular weight. Such increased viscosity and lubricity provide added comfort to the lens wearer when he or she places the disinfected lens into his or her eye. Thus, the presently useful high molecular weight barrier materials reduce foam formation during hydrogen peroxide destruction and preferably enhance the comfort experienced in wearing the disinfected lens. Moreover, this combination of advantages is obtained without modifying in any substantial manner the currently practiced method of contact lens disinfection using hydrogen peroxide. That is to say, the ultimate user of the present system is able to disinfect his/her contact lenses using the present system with little or no change from how he/she currently disinfects contact lenses with hydrogen peroxide. The only changes that become apparent are reduced foam formation and increased comfort in wearing the disinfected lenses. In one useful embodiment, no other lubricating agent and/or viscosity building or inducing agent and/or conditioning/ wetting agent is employed in the present compositions.

An illustrative HPDC-containing core formulation, e.g., tablet, may have the following composition:

|  | Wt. % |
| --- | --- |
| HPDC | 1–30 |
| Filler | 15–90 |
| Tonicity Agent | 1–90 |
| Buffering Agent | 1–50 |
| Lubricating Agent | 0–30 |

Useful tonicity agents include, but are not limited to, sodium chloride, potassium chloride, mannitol, dextrose, glycerin, propylene glycol and mixtures thereof.

Useful buffering agents include, but not limited to, acetate buffers, citrate buffers, phosphate buffers and borate buffers. Acids and bases may be used to adjust the pH of the present compositions as needed.

Useful lubricating agents include, but are not limited to, polyalkylene glycols, such as polyethylene glycols, preferably having molecular weights in the range of about 500 to about 10,000. Other materials conventionally used as lubricants in ophthalmically acceptable tablets may be employed in the present invention.

The inclusion of one or more of such other components in the present compositions may be important to facilitate the functioning of such compositions and the present methods. For example, it may be desirable to maintain the pH and/or osmolality of the liquid aqueous medium within certain ranges, for example, to obtain preferred enzyme activities, barrier component solubility and/or physiological acceptance. One or more of such other components may be included in the mixture which is applied to the item or items and which remain in the coated item or items. Also, such other component or components may be included in the present compositions separate and apart from the coated item or items.

In a useful embodiment, the HPDC is combined with at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et al U.S. Pat. RE 32,672 and Karageozian et al U.S. Pat. No. 3,910,296 are useful in the present invention. Each of these patents is incorporated in its entirety by reference herein. Among the useful enzymes are those selected from proteolytic enzymes, lipases, carbolytic enzymes and mixtures thereof.

Preferred proteolytic enzymes are those which are substantially free of sulfhydryl groups or disulfide bonds, whose presence may react with the active oxygen in the HPLM to the detriment of the activity of the enzyme. Metalloproteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Aspergillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213–249 (1970) and Deayl, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two subclasses, Subtilisin A and Subtilisin B. In the Subtilisin A grouping are enzymes derived from such species are *B. subtilis, B. licheniformis* and *B. pumilis*. Organisms in this sub-class produce little or no neutral protease or amylase. The Subtilisin B sub-class is made up of enzymes from such organisms a *B. subtilis, B. subtilis* var. *amylosacchariticus, B. amylolicuefaciens* and *B. subtilis* NRRL B3411. These organisms produce neutral proteases and amylases on a level about comparable to their alkaline protease production. One or more enzymes from the Subtilisin A sub-class are particularly useful.

In addition, other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.002 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

The HPDC-containing item or items are provided with a delayed release coating, a barrier coating. The present barrier coating can be formulated and applied so that the amount of time after the composition is introduced into the HPLM but before any HPDC is released in the HPLM is very effectively controlled. After this period of time, the barrier coating is dissolved into the HPLM sufficiently to rapidly release HPDC, preferably sufficient HPDC to destroy substantially all the remaining or residual hydrogen peroxide in the HPLM. The present compositions are preferably formulated and structured to delay the release of the HPDC in the HPLM for a time sufficient to effectively disinfect a contact lens and then release the HPDC in the HPLM for rapid and predictable destruction of the residual hydrogen peroxide.

The present delayed release barrier component may be applied using any suitable technique or combination of techniques, many of which are conventional and well known in the art. A particularly useful methodology for providing the present coating is as set forth in Park et al U.S. Pat. No. 5,145,644, the disclosure of which is incorporated in its entirety herein by reference. Briefly, this methodology provides for a barrier coating derived from a mixture comprising water, a ketone component and the water soluble coating materials. This mixture is applied to the HPDC-containing item or items in an amount sufficient to coat the item or items, in particular substantially all of the item or items, and form a precoated item or items. At least portions of the water and ketone component are removed from the precoated item or items to form the coated item or items, the item or items with a barrier coating.

In a particularly useful embodiment, one or more cleaning enzymes, as described above, are included in the mixture so that the barrier coating includes an amount of such enzyme or enzymes effective to remove at least one type of debris from a contact lens when released into the HPLM. Particularly useful enzymes for this embodiment of the present invention are peroxide-active proteolytic enzymes, such as those described in Huth et al U.S. Pat. RE 32,672. Subtilisin A is an especially useful cleaning enzyme for inclusion in the present mixture and barrier coating.

Alternately, the coated item or items can be further coated with a cleaning enzyme-containing outer coating to form an outer coated item or outer coated items structured to release the cleaning enzyme in the HPLM relatively shortly after, or even substantially at the same time as, the outer coated item or items are initially contacted with the HPLM. In this embodiment, the cleaning enzyme is located separate and apart from the main barrier coating of the composition. The outer coating can be derived by combining the cleaning enzyme with another quantity of the above-noted ketone-containing mixture, applying this combined mixture to the coated item or items and removing at least a portion of the water and ketone component or components. The cleaning enzyme can be applied to the coated item or items by itself or together with a material other than the presently useful water soluble coating components. For example, other water soluble materials may be combined with the cleaning enzyme and applied to the coated item or items to form the outer coated item or items. However, in one useful embodiment, the cleaning enzyme is applied to the coated item or items as a mixture comprising water, a ketone component, the cleaning enzyme or enzymes and one or more of the presently useful coating components.

The present method of disinfecting a lens, preferably a contact lens, includes contacting the lens to be disinfected with a HPLM at effective lens disinfecting conditions. The HPLM is contacted with a composition which includes a coated item or items containing a HPDC and a barrier coating, such as described herein. Using this method, the lens is disinfected and the residual hydrogen peroxide in the HPLM is effectively destroyed. Thus, after the HPDC has been released in the HPLM and acts to effectively destroy the residual hydrogen peroxide, the lens can be safely and comfortably taken directly from the liquid medium in which it was disinfected. If, as is preferred, the contact lens is enzymatically cleaned in addition to being disinfected, the cleaned/disinfected lens is preferably rinsed free of the cleaning enzyme or enzymes before being placed in the eye.

In a particularly useful embodiment, the contact lens to be disinfected is placed into the HPLM at substantially the same time as in the present composition. After a predetermined period of time, during which the contact lens is disinfected, the HPDC is released in the HPLM and effectively destroys the residual hydrogen peroxide.

In the event that a debris removing or cleaning enzyme is present in the composition, the contact lens in the liquid medium is also effectively cleaned of at least one type of debris. This cleaning action can occur either at the time the lens is being disinfected, e.g., if the enzyme is released in the HPLM when the composition is initially contacted with the HPLM or shortly thereafter or before the HPDC is released in the HPLM; or after the lens is disinfected, e.g., if the enzyme is released into the HPLM when the HPDC is released in the HPLM or thereafter. Preferably, the lens is cleaned at the time it is being disinfected.

It is preferred that the HPDC not be released in the HPLM until the lens has been immersed in the HPLM for a time sufficient, more preferably in the range of about 1 minute to about 4 hours and still more preferably in the range of about 5 minutes to about 1 hour, to effectively disinfect the lens. It is also preferred that substantially all of the residual hydrogen peroxide in the HPLM be destroyed in less than about 3 hours, more preferably in less than about 1 hour and still more preferably in less than about 30 minutes, after the HPDC is initially released into the HPLM.

The disinfecting contacting preferably occurs at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs at or about atmospheric pressure. This contacting preferably occurs for a time to substantially completely disinfect the lens being treated. Such contacting times can be in the range of about 1 minute to about 12 hours or more.

The following non-limiting examples illustrate certain aspects of the present invention.

EXAMPLE 1

A two layer tablet, having a core tablet surrounded by a coating, is prepared for testing. The core tablet and coating had the following compositions:

| CORE TABLET | |
|---|---|
| Crystalline catalase | (1) |
| Sodium chloride | 89.4 mg |
| Dibasic sodium phosphate (anhydrous) | 12.5 mg |
| Monobasic sodium phosphate monohydrate | 0.87 mg |
| Polyethylene glycol (molecular weight of about 3350) | 1.05 mg |
| COATING | |
| Hydroxypropylmethyl cellulose[2] | 3 to 6 mg |
| Polyethylene glycol (molecular weight of about 3350) | [3] |

[1]Catalase obtained as the result of the action of *Aspergillus niger*. This material is obtained from NOVO. The amount of catalase to be included is determined by an assay of the batch of product to be used. The tablet to be prepared contains about 1000 International Units of catalase activity.
[2]Material has a molecular weight of about 80,000 and a methoxyl substitution of about 28–30% and a hydroxypropoxyl substitution of about 7–12%.
[3]Present in the coating in an amount of about 20% by weight of the hydroxypropylmethyl cellulose. The polyethylene glycol in the coating is effective to facilitate solubilizing the hydroxypropylmethyl cellulose.

The coating is applied to the core tablet as follows. The hydroxypropylmethyl cellulose and polyethylene glycol in the coating are dissolved in a liquid vehicle containing 92% (v/v) acetone and 8% (v/v) water. The final formulation includes about 2% (w/v) hydroxypropylmethyl cellulose. Using a conventional coating system, the core tablet is coated with the final formulation. After drying to remove water and acetone, the layered or coated tablet includes sufficient hydroxypropylmethyl cellulose and polyethylene glycol to provide the desired delayed release characteristics without unduly adversely affecting, e.g., deactivating, the catalase in the core.

EXAMPLE 2

A three layer tablet, having a core tablet surrounded by two coating layers, is prepared for testing. The core tablet and coating having compositions similar to that described in Example 1.

The coating is applied to the core tablet as follows. A first formulation is derived by dissolving hydroxypropylmethyl cellulose and the polyethylene glycol in the coating in a liquid vehicle containing 92% (v/v) acetone and 8% (v/v) water. This first formulation includes about 2% (w/v) hydroxypropylmethyl cellulose. A second formulation is derived by dissolving hydroxypropylmethyl cellulose and Subtilisin A enzyme in the above-noted liquid vehicle. This second formulation includes about 2% (w/v) hydroxypropylmethyl cellulose and 0.05 to 0.1 units/ml Subtilisin A enzyme. Using a conventional coating system, the core tablet is coated with the first formulation. After drying, the two layered tablet is sprayed with the second formulation using the above-noted system. After drying, the three (3) layer tablet includes sufficient Subtilisin A enzyme to clean a contact lens of proteinaceous debris, and sufficient hydroxypropylmethyl cellulose and polyethylene glycol to provide the desired delayed release characteristics without unduly adversely affecting, e.g., deactivating, the catalase in the core.

EXAMPLE 3

A layered tablet in accordance with Example 1 is used to disinfect a conventional soft contact lens as follows. 10 ml of a 3% (w/v) aqueous solution of hydrogen peroxide is provided at room temperature. The contact lens to be disinfected and the layered tablet are placed in the solution at the same time. The solution bubbles for approximately one hour. After this period of time, the solution becomes and remains quiet. Substantially no foam exists after the bubbling stops. In addition, the viscosity of the remaining solution is measured and determined to be increased relative to the viscosity of the original aqueous solution of hydrogen peroxide.

Four hours after the contact lens is first introduced into the solution, it is removed from the solution and placed directly into the wearer's eye. It is found that after four hours the contact lens is effectively disinfected. Also, the lens wearer experiences no discomfort or eye irritation from wearing the disinfected contact lens. The bubbling of the solution provides a indication that hydrogen peroxide destruction is occurring. An indication that the peroxide destruction is substantially complete is provided when the bubbling stops.

EXAMPLE 4

A layered tablet in accordance with Example 2 is used to disinfect and clean a protein-based debris laden soft contact lens as follows. 10 ml of a 3% (w/v) aqueous solution of hydrogen peroxide is provided at room temperature. The contact lens to be disinfected and cleaned and the enzyme-containing layered tablet are placed in the solution at the same time. The solution bubbles for approximately one hour. After this period of time, the solution becomes and remains quiet. Substantially no foam exists after the bubbling stops. In addition, the viscosity of the remaining solution is measured and determined to be increased relative to the viscosity of the original aqueous solution of hydrogen peroxide.

Six hours after the contact lens is first introduced into the solution, it is removed from the solution, rinsed with physiological saline solution to remove the Subtilisin A and placed into the wearer's eye. It is found that after six hours, the contact lens is effectively disinfected and cleaned of protein-based debris. The lens wearer experiences no discomfort or eye irritation from wearing the disinfected and cleaned contact lens.

EXAMPLE 5

A first series of coated tablets are selected for testing. These tablets are commercially available and are sold by Allergan under the trademark Oxysept. Each of these tablets includes about 5200 International Units of catalase activity derived from catalase obtained as the result of *Micrococcus luteus*. The coating of each of these tablets includes about 8 milligrams of hydroxypropylmethyl cellulose having a molecular weight of about 10,000.

A second series of tablets are prepared for testing. These tablets are similar to the tablets of the first series except that the hydroxypropylmethyl cellulose used is a mixture of 72% by weight of hydroxypropylmethyl cellulose having a molecular weight of about 80,000, a methoxyl substitution of about 28 to 30% and a hydroxypropoxyl substitution of about 7 to 12%, and 28% by weight of hydroxypropylmethyl cellulose having a molecular weight of about 30,000 at a methoxyl substitution of about 19 to 24% and a hydroxypropoxyl substitution of about 7 to 12%

The tablets are tested as follows. For each tablet 10 ml of a commercially available solution containing 3% (w/v) of hydrogen peroxide is placed in a 100 ml graduated cylinder. The tablet is then added to the graduated cylinder and the maximum amount of foaming is observed and recorded.

Results of these tests are as follows:

| First Tablet | Maximum Foaming ml | Second Tablet | Maximum Foaming ml |
|---|---|---|---|
| 1 | 18 | 1 | 4 |
| 2 | 30 | 2 | 4 |
| 3 | 25 | 3 | 4 |
| 4 | 32 | 4 | 2 |
| 5 | 18 | 5 | 5 |
| 6 | 15 | 6 | 4 |
| 7 | 8 | 7 | 4 |
| 8 | 15 | 8 | 5 |
| 9 | 12 | 9 | 4 |
| 10 | 18 | 10 | 3 |

In each case substantially all the hydrogen peroxide initially present in the solution is destroyed.

These results demonstrate the unexpectedly large reduction in the foaming characteristics of delayed release tablets coated with materials having high molecular weights. In addition, the small amount of foaming obtained using the high molecular weight coating material (second tablets) is more consistent (within 2 ml) than the foaming obtained using the low molecular weight material (first tablets). Such reduced, consistent amount of foaming is highly advantageous, making disinfecting contact lenses more convenient and reducing the risk that liquid will leak from the container during the contact lens disinfecting/hydrogen peroxide destruction processing.

EXAMPLE 6

A series of coated tablets are prepared for testing. Each of these include a core containing 5,200 International Units of catalase activity derived from catalase obtained as the result of the action of *Micrococcus luteus*.

The control tablet is similar to the first series of tablets identified as the first series of tablets in Example 5.

Tablet 1 is similar to the control tablet except that the coating includes about 3–8 mg of hydroxypropylmethyl cellulose having a molecular weight of about 80,000, a methoxyl substitution of about 28 to 30% and a hydroxypropoxyl substitution of about 7 to 12%.

Tablets 2 and 3 are similar to the control tablet except that the coating includes about 4–5 mg of hydroxypropylmethyl cellulose having a molecular weight of about 80,000, a methoxyl substitution of about 28 to 30% and a hydroxypropoxyl substitution of about 7 to 12%.

Tablets 4 to 7 are similar to tablets 2 and 3 except that the coating includes 10% by weight (Tablets 4 and 5), 20% by weight (Tablet 6), and 32% by weight (Tablet 7) of hydroxypropylmethyl cellulose having a molecular weight of about 30,000, a methoxyl substitution of about 19 to 24% and a hydroxypropoxyl substitution of about 7 to 12%.

Each of these tablets are placed in 10 of the HPLM referred to in Example 5. After the coating is completely dissolved, the hydrogen peroxide is destroyed and the temperature is stable at 25° C., the viscosity of the resulting liquid is measured. Duplicate tests are performed.

Results of these tests are as follows:

| Tablet | Viscosity, cps | Duplicate Viscosity, cps |
|---|---|---|
| Control | 1.16 | 1.15 |
| 1 | 1.33 | 1.33 |
| 2 | 1.50 | 1.50 |
| 3 | 1.50 | 1.50 |
| 4 | 1.52 | 1.52 |
| 5 | 1.51 | 1.52 |
| 6 | 1.47 | 1.47 |
| 7 | 1.43 | 1.43 |

These results demonstrate that the use of soluble coating materials having high molecular weights advantageously provide increased viscosity, and therefore increased lubricity, to liquid media after hydrogen peroxide destruction. Thus, the need for additional viscosity modifiers and/or lubricants is reduced or even eliminated. Also, by properly selecting the high molecular weight soluble coating material, the viscosity of the resulting liquid medium can be controlled, as desired.

In summary, the present invention provides for effective contact lens disinfection and effective HPDC destruction. These results are achieved with reduced foaming and advantageously increased viscosity and lubricity. Moreover, user compliance is greatly facilitated, for example, because the present system can be used, by the lens wearer, in substantially the exact same way as he/she currently disinfects his/her contact lens with hydrogen peroxide.

While this invention has been described with respect to various specific examples and embodiments, it is to be understood that the invention is not limited thereto and that it can be variously practiced within the scope of the following claims.

What is claimed is:

1. A composition comprising a hydrogen peroxide destroying component effective when released in a hydrogen peroxide-containing liquid aqueous medium to destroy or cause the destruction of hydrogen peroxide present in the hydrogen peroxide-containing liquid aqueous medium, and a barrier component acting to substantially prevent the release of said hydrogen peroxide destroying component for a period of time after said composition is initially contacted with the hydrogen peroxide-containing liquid aqueous medium, said barrier component comprising a material selected from the group consisting of water soluble cellulose derivatives and mixtures thereof having a molecular weight of at least about 20,000, said composition resulting in reduced foam formation relative to a similar composition including a barrier component comprising a similar material having a molecular weight of 10,000 when both said composition and said similar composition are exposed to identical hydrogen peroxide-containing liquid aqueous media to destroy or cause the destruction of the hydrogen peroxide therein.

2. The composition of claim 1 wherein said material has a molecular weight of at least about 60,000, and said composition being effective to increase the viscosity and lubricity of an aqueous liquid in which said material is dissolved.

3. The composition of claim 1 wherein said material is hydroxypropylmethyl cellulose.

4. The composition of claim 1 wherein said barrier component further includes an effective amount of a component useful in said composition to facilitate solubilizing said material.

5. The composition of claim 1 wherein said hydrogen peroxide destroying component includes catalase.

6. The composition of claim 1 wherein said hydrogen peroxide destroying component includes catalase obtained as the result of the action of *Aspergillus niger*.

7. The composition of claim 1 which further comprises at least one enzyme capable of removing at least one type of debris from a contact lens located in the liquid aqueous medium.

8. The composition of claim 1 which has a layered structure with at least one item comprising said hydrogen peroxide destroying component substantially coated with a coating comprising said material.

9. The method of disinfecting a lens comprising:
  (1) contacting a lens with a hydrogen peroxide-containing liquid aqueous medium at effective lens disinfecting conditions, thereby disinfecting said lens; and
  (2) contacting said hydrogen peroxide-containing aqueous liquid medium with a composition comprising a hydrogen peroxide destroying component effective when released in said hydrogen peroxide-containing liquid aqueous medium to destroy or cause the destruction of hydrogen peroxide present in said hydrogen peroxide-containing liquid aqueous medium, and a barrier component acting to substantially prevent the release of said hydrogen peroxide destroying component for a period of time after said composition is initially contacted with said hydrogen peroxide-containing liquid aqueous medium, said barrier component comprising a material selected from the group consisting of water soluble cellulose derivatives and mixtures thereof having a molecular weight of at least about 20,000, said contacting of step (2) resulting in less foam formation relative to a similar contacting using a similar composition including a barrier component comprising a similar material having a molecular weight of 10,000.

10. The method of claim 9 wherein said material has a molecular weight of at least about 60,000.

11. The method of claim 9 wherein said material is hydroxypropylmethyl cellulose, and said step (2) further resulting in an increase in the viscosity and lubricity of the liquid aqueous medium in which said material is dissolved.

12. The method of claim 9 wherein said barrier component further includes an effective amount of a component useful to facilitate solubilizing said material during step (2).

13. The method of claim 9 wherein said hydrogen peroxide destroying component includes catalase obtained as the result of the action of *Aspergillus niger*.

14. The method of claim 9 wherein said composition further comprises at least one enzyme capable of removing at least one type of debris from a contact lens located in the liquid aqueous medium.

15. A composition comprising catalase obtained as the result of the action of *Aspergillus niger* effective when released in a hydrogen peroxide-containing liquid aqueous medium to cause the destruction of hydrogen peroxide present in the hydrogen peroxide-containing liquid aqueous medium, and a barrier component acting to substantially prevent the release of said catalase for a period of time after said composition is initially contacted with the hydrogen peroxide-containing liquid aqueous medium, said barrier component comprising a material selected from the group consisting of water soluble cellulose derivatives and mixtures thereof having a molecular weight of at least about 20,000, said composition resulting in reduced foam formation relative to a similar composition including a barrier component comprising a similar material having a molecular weight of 10,000 when both said composition and said similar composition are exposed to identical hydrogen peroxide-containing liquid aqueous media to destroy or cause the destruction of the hydrogen peroxide therein.

16. The composition of claim 15 wherein said material is hydroxypropylmethyl cellulose.

17. The composition of claim 15 which is in the form of a tablet and includes about 50 to about 2000 International Units of catalase activity from said catalase obtained as the result of the action of *Aspergillus niger*.

18. The composition of claim 15 which further comprises at least one enzyme capable of removing at least one type of debris from a contact lens located in the liquid aqueous medium, said composition including an effective amount of said at least one enzyme to substantially remove at least one type of debris from a debris laden contact lens located in the liquid aqueous medium in which said at least one enzyme is released.

* * * * *